United States Patent [19]

Chavdarian

[11] Patent Number: 4,683,225
[45] Date of Patent: Jul. 28, 1987

[54] O-(SUBSTITUTED) BENZYL DITHIOPHOSPHONATE INSECTICIDES

[75] Inventor: Charles G. Chavdarian, Martinez, Calif.

[73] Assignee: Stauffer Chemical Company, Westport, Conn.

[21] Appl. No.: 792,087

[22] Filed: Oct. 28, 1985

[51] Int. Cl.$^4$ .......................... A01N 57/06; C07F 9/40
[52] U.S. Cl. ..................... 514/128; 514/141; 558/197; 558/214
[58] Field of Search ................ 558/214, 197; 514/128, 514/141

[56] References Cited

U.S. PATENT DOCUMENTS 3,780,143 12/1973 Gutman ............................... 558/214
3,995,032 11/1976 Gutman ............................... 558/214

FOREIGN PATENT DOCUMENTS 1132132 6/1962 Fed. Rep. of Germany .
1139492 11/1962 Fed. Rep. of Germany .

OTHER PUBLICATIONS

Eliseenkoua et al., "Izv. Akad. Nauk. USSR," (1972), No. 12, pp. 2690–2694.

Primary Examiner—Anton H. Sutto
Attorney, Agent, or Firm—Joel G. Ackerman

[57] ABSTRACT

Compounds having the formula

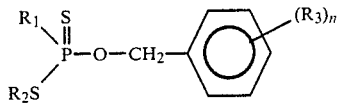

in which $R_1$ is methyl or ethyl; $R_2$ is $C_1$–$C_6$ alkyl; $R_3$ is halogen, $C_1$–$C_4$ alkyl, trifluoromethyl, thio-($C_1$–$C_4$ alkyl) or phenoxy, and n is 0, 1 or 2; provided that if $R_2$ is methyl, then $R_1$ is methyl, are insecticides.

52 Claims, No Drawings

O-(SUBSTITUTED) BENZYL DITHIOPHOSPHONATE INSECTICIDES

This invention relates to a series of dithiophosphonate insecticides having the formula

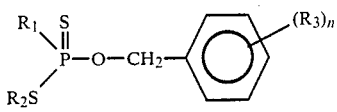

in which $R_1$ is methyl or ethyl; $R_2$ is $C_1$–$C_6$ alkyl; $R_3$ is halogen, $C_1$–$C_4$ alkyl, trifluoromethyl, thio-($C_1$–$C_4$ alkyl) or phenoxy, and n is 0, 1 or 2; provided that if $R_2$ is methyl, then $R_1$ is methyl.

The term "alkyl" refers to straight or branched chain saturated aliphatic moieties, such as methyl, ethyl, n-propyl, isopropyl, sec.butyl, tert.-butyl and the like. The term "halogen" includes fluoro, chloro, bromo and iodo.

The substituent $R_2$ may be methyl, if $R_1$ is also methyl, but is preferably a $C_3$–$C_6$ alkyl group and most preferably $C_4$–$C_6$ alpha-branched alkyl such as secondary or tertiary butyl, 1,1-dimethylpropyl (tertiary amyl) and the like. The substituent $R_3$ may be at any position or positions on the phenyl ring. When n=0, the phenyl ring is unsubstituted.

The term "insects" as used herein refers to the broad and commonly understood usage rather than to those creatures which in the strict biological sense are classified as insects, and includes, in addition to those belonging to the class *Insecta*, some classes of acarids such as spiders, mites, ticks, and the like, particularly mites.

The compounds of this invention have demonstrated activity against a number of insect species, and generally show particularly good activity against insects which attack foliage, such as larvae of lepidoptera.

The compounds of the present invention were prepared by two methods, designated methods (A) and (B) below.

METHOD (A)

In this procedure the appropriate S-alkyl phosphonodithioic halide (preferably chloride) is reacted with a suitable benzyl alkoxide according to the equation:

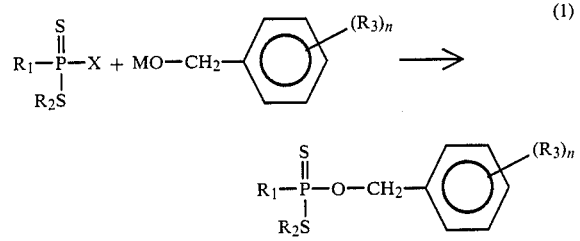

in which $R_1$–$R_3$ and n are as defined above, X stands for halogen, preferably chlorine or bromine, and M stands for an alkali metal, preferably sodium or potassium.

Reaction (1) is generally carried out at a temperature of from about 0° to about 70° C., preferably from about 0° to about 25° C., in an organic solvent. Suitable solvents include aromatic hydrocarbons such as benzene or toluene and ethers such as diethylether, 1,2-dimethoxyethane, or tetrahydrofuran (the preferred solvent). The benzyl alkoxide is produced by reaction of a benzylic alcohol with an alkali metal-containing base. Suitable bases include sodium and potassium hydride, with sodium hydride preferred. The desired product can be recovered and purified by evaporation of solvent and chromatography.

The S-alkyl phosphonodithioic halide may be prepared by any conventional means, such as by reaction of an alkyl mercaptan with an alkylphosphonothioic dihalide as described in U.S. Pat. No. 4,258,038 or by reaction of an alkyl mercaptan with an alkyl dihalophosphine, followed by reaction with hydrogen sulfide, as described in Akamsin, et al., *Chemical Abstracts*, Vol. 68, No. 29783x (1968).

The process of this invention is preferable for S-tertiary and secondary alkyl compounds, but less so for other S-alkyl phosphonodithioic halides; low yields or mixtures of difficultly separable products may result.

METHOD (B)

This procedure involves the sequential reaction of the appropriate alkyl thinophosphine sulfide, first with a benzylic alcohol in the presence of a base, and then with an alkyl halide:

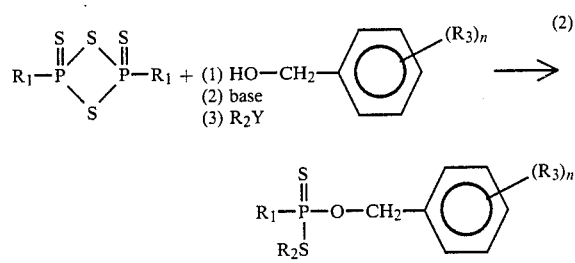

in which $R_1$–$R_3$ and n are as defined above and Y is a halogen, preferably bromine or iodine.

This method can be used for preparation of all compounds of this invention except those in which $R_2$ is a tertiary alkyl group.

The starting material sulfides for reaction (2) may be obtained by the procedure described in P. E. Newallis, et al., *Journal of Organic Chemistry*, 1962, Vol. 27, p. 3829.

The process is generally carried out at a temperature of from about 0° to about 110° C., preferably from about 0° to about 70° C., in a organic solvent. Suitable solvents include aromatic hydrocarbons such as benzene or toluene, ethers such as diethyl ether, 1,2-dimethoxyethane, or tetrahydrofuran (preferred) and nitriles such as acetonitrile. Suitable bases are tertiary amines such as triethylamine (preferred), dimethylaniline, diethylaniline and pyridine. Inorganic bases such as sodium or potassium carbonate may be used. The product may be recovered by evaporation of the solvent and purified by chromatography or distillation.

The following represent examples of the preparation of compounds of this invention.

EXAMPLE 1

Preparation of O-(2-Fluorobenzyl) S-t-butylethylphosphonodithioate (Compound 43 herein, Method A)

To a slurry of 0.35 grams (g) (0.0146 mole) of oil-free sodium hydride in 15 milliliters (ml) of tetrahydrofuran under nitrogen and at room temperature was added dropwise 1.75 g (0.0138 mole) of 2-fluorobenzyl alcohol. After stirring for 45 minutes, the mixture was cooled to 0° and a solution of 3.0 g (0.0138 mole) of S-t-butyl ethylphosphonodithioic chloride in 5 ml of tetrahydrofuran was added dropwise and the mixture quenched with 10 ml of water and extracted with ether (3×10 ml). The etheral layers were combined and washed with 20 ml of water and 20 ml of saturated sodium chloride, dried with magnesium sulfate, and evaporated to produce 4.15 g of an oil. Purification with a preparative, centrifugally-accelerated, thin-layer chromatograph (4 mm thick silica gel with 98:2 hexane-acetone as eluent) afforded 3.03 g (72% of theoreticl yield) of the title compound, a clear, mobile oil. The structure was confirmed by nuclear magnetic resonance, infrared and mass spectroscopy.

EXAMPLE 2

Preparation of O-(4-Chlorobenzyl) S-n-propyl ethylphosphonodithioate (Compound 56 herein, Method B)

To a slurry of 1.86 g (0.0075 mole) of ethylthionophosphine sulfide in 20 ml of tetrahydrofuran under nitrogen and at room temperature was added 2.14 g (0.015 mole) of 4-chlorobenzyl alcohol. After the sulfide had completely dissolved, 2.3 ml (1.67 g, 0.0165 mole) of triethylamine was added, followed by the addition of 1.50 ml (2.03 g, 0.0165 mole) of 1-bromopropane. The mixture was refluxed for 2 hours. The mixture was quenched with water and extracted with ether. The ethereal solution was washed with saturated sodium chloride, dried with magnesium sulfate, and evaporated to 4.34 g of an oil. Purification with a preparative, centrifugally-accelerated, thin-layer chromatograph (4 mm thick silica gel with 98:2 hexane-acetone as eluent) afforded 3.32 g (72% of theoretical yield) of the title compound, a clear, mobile oil. The structure was confirmed by nuclear magnetic resonance, infrared, and mass spectroscopy.

The following Table I depicts representative compounds of this invention, which may be prepared by the processes previously described. Structures of these compounds were confirmed by analysis as above. Those compounds for which an asterisk (*) appears in the column designated $(R_3)_n$ had no substitution on the phenyl ring.

TABLE I

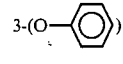

| Compound Number | $R_1$ | $R_2$ | $(R_3)_n$ | $n_D^{30}$ | Method |
|---|---|---|---|---|---|
| 1 | $CH_3$ | $t\text{-}C_4H_9$ | * | 1.5734 | A |
| 2 | $C_2H_5$ | $s\text{-}C_4H_9$ | 2-Br | 1.5817 | A |
| 3 | $C_2H_5$ | $s\text{-}C_4H_9$ | 2-F | 1.5508 | A |
| 4 | $C_2H_5$ | $s\text{-}C_4H_9$ | 2,4-Cl | 1.5746 | A |
| 5 | $CH_3$ | $t\text{-}C_4H_9$ | 2,6-Cl | 1.5878 | A |
| 6 | $CH_3$ | $t\text{-}C_4H_9$ | 3,4-Cl | 1.5890 | A |
| 7 | $C_2H_5$ | $s\text{-}C_4H_9$ | 3,4-Cl | 1.5773 | A |
| 8 | $C_2H_5$ | $s\text{-}C_4H_9$ | 2,6-Cl | 1.5780 | A |
| 9 | $C_2H_5$ | $n\text{-}C_3H_7$ | * | 1.5700 | B |
| 10 | $CH_3$ | $n\text{-}C_3H_7$ | * | 1.5757 | B |
| 11 | $CH_3$ | $CH_3$ | * | 1.5961 | B |
| 12 | $CH_3$ | $t\text{-}C_4H_9$ | 2-F | 1.5612 | A |
| 13 | $CH_3$ | $t\text{-}C_4H_9$ | 2,5-Cl | 1.5909 | A |
| 14 | $C_2H_5$ | $s\text{-}C_4H_9$ | 2,5-Cl | 1.5767 | A |
| 15 | $CH_3$ | $t\text{-}C_4H_9$ | 2-Br | 1.5969 | A |

TABLE I-continued

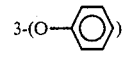

| Compound Number | $R_1$ | $R_2$ | $(R_3)_n$ | $n_D^{30}$ | Method |
|---|---|---|---|---|---|
| 16 | $C_2H_5$ | $t\text{-}C_4H_9$ | * | 1.5684 | A |
| 17 | $CH_3$ | $t\text{-}C_4H_9$ | 3-F | 1.5587 | A |
| 18 | $CH_3$ | $t\text{-}C_4H_9$ | 4-F | 1.5585 | A |
| 19 | $CH_3$ | $s\text{-}C_4H_9$ | * | 1.5687 | A |
| 20 | $C_2H_5$ | $s\text{-}C_4H_9$ | * | 1.5619 | A |
| 21 | $CH_3$ | $t\text{-}C_5H_{11}$ | * | 1.5721 | A |
| 22 | $CH_3$ | $t\text{-}C_4H_9$ | 3,4-$CH_3$ | 1.5692 | A |
| 23 | $C_2H_5$ | $s\text{-}C_4H_9$ | 4-($t\text{-}C_4H_9$) | 1.5486 | A |
| 24 | $CH_3$ | $t\text{-}C_4H_9$ | 2-$CF_3$ | 1.5289 | A |
| 25 | $CH_3$ | $s\text{-}C_4H_9$ | 3,4-Cl | 1.5826 | A |
| 26 | $CH_3$ | $s\text{-}C_4H_9$ | 2-F | 1.5567 | A |
| 27 | $CH_3$ | $s\text{-}C_4H_9$ | 3-F | 1.5543 | A |
| 28 | $CH_3$ | $s\text{-}C_4H_9$ | 4-F | 1.5541 | A |
| 29 | $CH_3$ | $t\text{-}C_4H_9$ | 2-Cl | 1.5811 | A |
| 30 | $CH_3$ | $t\text{-}C_4H_9$ | 3-Cl | 1.5802 | A |
| 31 | $CH_3$ | $t\text{-}C_4H_9$ | 4-Cl | 1.5810 | A |
| 32 | $CH_3$ | $t\text{-}C_4H_9$ | 3-$CF_3$ | 1.5269 | A |
| 33 | $CH_3$ | $t\text{-}C_4H_9$ | 4-$SCH_3$ | 1.5988 | A |
| 34 | $C_2H_5$ | $s\text{-}C_4H_9$ | 4-$SCH_3$ | 1.5928 | A |
| 35 | $C_2H_5$ | $s\text{-}C_4H_9$ | 3-F | 1.5549 | A |
| 36 | $C_2H_5$ | $t\text{-}C_4H_9$ | 4-F | 1.5542 | A |
| 37 | $CH_3$ | $t\text{-}C_4H_9$ | 4-($t\text{-}C_4H_9$) | 1.5559 | A |
| 38 | $CH_3$ | $t\text{-}C_4H_9$ | 3-(O—⌬) | 1.5964 | A |
| 39 | $CH_3$ | $s\text{-}C_4H_9$ | 3-(O—⌬) | 1.5908 | A |
| 40 | $C_2H_5$ | $t\text{-}C_5H_{11}$ | * | 1.5661 | A |
| 41 | $C_2H_5$ | $t\text{-}C_4H_9$ | 3-$CF_3$ | 1.5245 | A |
| 42 | $C_2H_5$ | $s\text{-}C_4H_9$ | 3-$CF_3$ | 1.5226 | A |
| 43 | $C_2H_5$ | $t\text{-}C_4H_9$ | 2-F | 1.5564 | A |
| 44 | $C_2H_5$ | $t\text{-}C_4H_9$ | 4-Cl | 1.5739 | A |
| 45 | $C_2H_5$ | $t\text{-}C_4H_9$ | 3,4-Cl | 1.5827 | A |
| 46 | $CH_3$ | $t\text{-}C_4H_9$ | 2-Cl, 6-F | 1.5708 | A |
| 47 | $CH_3$ | $t\text{-}C_4H_9$ | 2,5-F | 1.5494 | A |
| 48 | $CH_3$ | $s\text{-}C_4H_9$ | 3-$CF_3$ | 1.5264 | A |
| 49 | $CH_3$ | $t\text{-}C_4H_9$ | 3,4-F | 1.5491 | A |
| 50 | $CH_3$ | $s\text{-}C_4H_9$ | 4-Cl | 1.5737 | A |
| 51 | $CH_3$ | $s\text{-}C_4H_9$ | 4-(O—⌬) | 1.5907 | A |
| 52 | $CH_3$ | $i\text{-}C_3H_7$ | * | 1.5747 | B |
| 53 | $CH_3$ | $i\text{-}C_3H_7$ | 3-F | 1.5586 | B |
| 54 | $C_2H_5$ | $i\text{-}C_3H_7$ | 3-$CF_3$ | 1.5220 | B |
| 55 | $CH_3$ | $n\text{-}C_3H_7$ | 4-F | 1.5608 | B |
| 56 | $C_2H_5$ | $n\text{-}C_3H_7$ | 4-Cl | 1.5765 | B |
| 57 | $CH_3$ | $n\text{-}C_3H_7$ | 3-F | 1.5605 | B |
| 58 | $CH_3$ | $t\text{-}C_4H_9$ | 2,4-F | 1.5491 | A |
| 59 | $CH_3$ | $t\text{-}C_4H_9$ | 3-Br | 1.5911 | A |
| 60 | $CH_3$ | $t\text{-}C_4H_9$ | 4-Br | 1.5925 | A |
| 61 | $C_2H_5$ | $s\text{-}C_4H_9$ | 4-Cl | 1.5687 | A |
| 62 | $CH_3$ | $t\text{-}C_4H_9$ | 4-$CF_3$ | 1.5296 | A |

*$n = 0$

Insecticidal Evaluation Tests

The compounds in Table I above were tested for insecticidal activity using the following testing procedures. LD-50 values, based on the results of these tests, and/or calculated according to dosage-mortality curves, are expressed in Table II.

Housefly [*Musca domestica*]

(a.) Contact: Test compounds were diluted in acetone and aliquots pipetted onto the bottom of aluminum dishes. To insure even spreading of the chemical on the bottom of the dishes, 1 ml of acetone containing 0.01% peanut oil was also added to each dish. After all solvents had evaporated, the dishes were placed in circular cardboard cages containing 25 female houseflies, 1-2 days old. The cages were covered on the bottom with cellophane and on the top with tulle netting, and each contained a sugar-water saturated cotton plug for maintenance of the flies. Mortality was recorded after 48 hours. Test levels ranged from 100 μg/25 female houseflies downward. The LD-50 values are expressed below in Table II under the heading "HF-C", in terms of μg of the test compound per 25 female flies.

(b.) Fumigant: Test compounds were diluted in acetone and aliquots pipetted onto 55 millimeter (mm) filter paper discs in the bottom of aluminum dishes. Immediately after the acetone had completely evaporated the dishes were placed in circular cardboard cages (volume—285 ml) containing 25 female houseflies. The cages were sealed on both ends with cellophane and each contained a sugar-water saturated cotton plug for maintenance of the flies. A piece of netting was placed over the aluminum dish in the cage in such a way that the flies were unable to come into direct contact with the chemically treated filter paper. Mortality was recorded after 48 hours. Test levels ranged from 100 μg/25 female houseflies downward. The LD-50 values are expressed in the following Table II under the heading "HF-F", in terms of μg of the test compound per 25 female houseflies per 285 ml volume of the test container.

Black Bean Aphid [*Aphis fabae* (Scop.)]

Nasturtium plants (*Tropaelum sp.*) approximately 5 cm tall, were transplanted into sandy loam soil in small cups and infested with 25-50 black bean aphids of mixed ages. Twenty-four hours later they were sprayed to the point of runoff with 50-50 acetone-water solutions of the test compounds. Treated plants were held in the greenhouse and mortality was recorded after 48 hours. Test concentrations ranged from 0.05% downward. The LD-50 values are expressed below in Table II under the heading "BA-C" in terms of percent of the test compound in the sprayed solution.

Tobacco Budworm [*Heliothis virescens* (Fabricius)]

(a) Contact: Test compounds were diluted in a 50-50 acetone-water solution. Cotton (*Gossypium sp.*) cotyledons were immersed in the test solutions for 2-3 seconds and placed on a wire screen to dry. The dried leaves were placed in petri dishes containing a moistened piece of filter paper and infested with 5 second-instar tobacco budworm larvae. The dishes were placed in a high humidity chamber for 5 days, and percent mortality of the larvae recorded. Test concentrations ranged from 0.1% downward. The LD-50 values are expressed below in Table II under the heading "TBW-C" in terms of percent of the test compound in the solution.

(b). Eggs: Paper towel patches of 2-day old eggs of the tobacco budworm were dipped in acetone solutions of the test compounds and placed in petri dishes containing a portion of larval rearing medium. Treated eggs were maintained at 78° F. and mortality was recorded after all control eggs had hatched and the young larvae were feeding on the media. Test concentrations ranged from 0.1% downward. The LD-50 values are expressed below in Table II under the heading "TBW-E" in terms of percent of the test compound in the solution.

Beet Armyworm (*Spodoptera exigua*)

Test compounds were diluted in a 50-50 acetone-water solution. Young leaves of sugar beets (*Beta vulgaris*) were immersed in the test solutions for 2-3 seconds and placed on a wire screen to dry. The dried leaves were placed in petri dishes containing a moistened filter paper and infested with five second-instar beet anyworm larvae. The dishes were placed in a high humidity chamber. Mortality of the larvae was recorded five days later. Test concentrations range from 0.1% downward. The LD-50 values are expressed below in Table II under the heading "BAW" in terms of percent of the test compound in solution.

Cabbage Looper [*Trichoplusia ni* (Hübner)]

Test compounds were diluted in a 50-50 acetone-water solution. Cotyledons of hyzini squash (*Calabacita abobrinha*), approximately 1×1.5 inches, were immersed in the test solutions for 2-3 seconds and placed on a wire screen to dry. The dried leaves were placed in petri dishes containing a moistened piece of filter paper and infested with 5 second-instar cabbage looper larvae. The dishes were placed in a high humidity chamber. Mortality of the larvae was recorded 5 days later. Test concentrations ranged from 0.1% downward. The LD-50 values are expressed below in Table II under the heading "CL" in terms of percent of the test compound in this solution.

Western Spotted Cucumber Beetle Larvae [*Dibrotica undecimpunctat undecimpunctata* (Mannherheim)]

Ten grams of moist potting soil was placed in a plastic cup. Test compounds were dissolved in acetone or an other appropriate solvent. A 0.05 ml aliquot of the test sample, diluted to the desired concentration, was added to the soil. The cup was capped and the soil was mixed on a vortex mixer for approximately 15 seconds. An indentation was made on the surface of the soil and approximately 50 *Diabrotica* eggs were added. The eggs were covered with soil and maintained at room temperature (approximately 70° F. or 21° C.). Four days later a section of Romaine lettuce (*Latuca sativa*) leaf was placed in the treated cups. One week later the cups were examined for live larvae. Test concentrations ranged from 25 ppm downward. The LD-50 values are expressed below in Table II under the heading "Diabrotica" in terms of ppm of the test compound in the soil.

Acaricidal Evaluation Test

The two-spotted mite (2SM) [*Tetranychus urticae* (Koch)] was employed in tests for miticides. The test procedure was as follows:

Pinto bean plants (*Phaseolus sp.*) approximately 10 cm tall, were transplanted into sandy loam soil in small cups and thoroughly infested with two-spotted mites of mixed ages and sexes. Twenty-four hours later the infested plants were inverted and dipped for 2-3 seconds in 50-50 acetone-water solutions of the test compounds. Treated plants were held in the greenhouse, and 7 days later mortality was determined for both adult mites and the nymphs hatching from eggs which were on the plants at the time of treatment. Test concentrations ranged from 0.05% downward. The LD-50 values are expressed below in Table II under the headings "2SM-A" (i.e., adults) and "2SM-E" (i.e. eggs) in terms of percent concentration of the test compound in the solution.

Systemic Evaluation Test

This test evaluates the root absorption and upward translocation of the candidate systemic compound. The two-spotted mite (2SM) [*Tetranychus urticae* (Koch)] and the bean aphid (BA) [*Aphis fabae* (Scop.)] were employed in the test for systemic activity. Tests were conducted as follows;

Two-Spotted Mite

Test compounds were dissolved in acetone and aliquots diluted in 200 ml of water in glass bottles. Two pinto beans plants (*Phaseolus sp.*), with expanded primary leaves, were supported in each bottle by cotton plugs so that their roots and stems were immersed in the treated water. The plants were then infested with 75–100 two-spotted mites of various ages and sexes. One week later the mortality of the adult mites and nymphs was recorded. Test concentrations of the chemicals in the water ranged from 10 ppm downward. The LD-50 values are expressed in Table II under the heading "2-SM (S)" in terms of ppm of the test compound in the solution.

Black Bean Aphid [*Aphis fabae* (Scop.)]

Nasturtium plants (*Tropaelum sp.*), approximately 5 cm tall, were transplanted into 400 grams of sandy loam soil in one pint containers. Test chemicals were dissolved in acetone and aliquots diluted in 50–60 ml of water. The treated water was poured onto the surface of the soil and allowed to thoroughly soak in. The treated plants were infested with 25–50 black bean aphids of mixed ages and held in the greenhouse. Mortality was recorded after three days. Test concentrations ranged from 10 ppm down to that at which 50% mortality occurs. The LD-50 values are expressed in Table II under the heading "BA(S)" in terms of ppm of the test compound in the soil.

TABLE II

| Cmpd. No. | HF, μg C | F* | BA C, % | S, ppm | 2-SM A, % | S, ppm | E, % | TBW, % C | E | BAW, % | CL, % | Diabrotica, ppm (soil) |
|---|---|---|---|---|---|---|---|---|---|---|---|---|
| 1 | >100 | >100 | 0.006 | 6 | 0.001 | 3 | 0.01 | 0.002 | 0.006 | 0.002 | 0.001 | 4 |
| 2 | 41 | >100 | 0.03 | >10 | 0.001 | >10 | 0.03 | 0.035 | 0.08 | 0.06 | 0.035 | >25 |
| 3 | 42 | >100 | 0.01 | 8 | 0.002 | >10 | 0.03 | 0.009 | 0.075 | 0.03 | 0.07 | 7.5 |
| 4 | >100 | >100 | 0.003 | >10 | 0.0003 | >10 | 0.006 | 0.006 | <0.1 | 0.06 | 0.02 | 7.5 |
| 5 | >100 | >100 | 0.01 | >10 | 0.002 | >10 | 0.03 | 0.03 | 0.04 | 0.005 | 0.006 | 2 |
| 6 | >100 | >100 | 0.006 | >10 | 0.002 | >10 | 0.006 | 0.002 | 0.002 | 0.007 | 0.002 | 7.5 |
| 7 | <30 | >10 | 0.002 | >10 | 0.001 | >10 | 0.006 | 0.009 | 0.03 | 0.009 | 0.005 | 17 |
| 8 | 50 | 70 | 0.003 | >10 | 0.006 | >10 | 0.03 | >0.1 | 0.05 | >0.1 | 0.06 | >25 |
| 9 | 10 | 25 | 0.006 | >10 | 0.05 | >10 | 0.01 | 0.004 | 0.03 | 0.08 | 0.006 | >25 |
| 10 | 17 | 60 | 0.001 | 6 | 0.05 | 6 | 0.003 | 0.005 | 0.002 | 0.03 | 0.002 | 3 |
| 11 | 10 | 13 | 0.0006 | 2 | 0.03 | 3 | 0.006 | 0.01 | 0.008 | >0.1 | 0.006 | 3 |
| 12 | >100 | >100 | 0.003 | >10 | 0.01 | >10 | 0.002 | 0.006 | 0.003 | 0.006 | 0.001 | 7.5 |
| 13 | >100 | >100 | 0.003 | >10 | 0.006 | >10 | 0.006 | 0.005 | 0.03 | 0.006 | 0.002 | 7.5 |
| 14 | 15 | >100 | 0.0006 | >10 | 0.003 | >10 | 0.01 | 0.006 | 0.04 | 0.006 | 0.006 | >25 |
| 15 | >100 | >100 | >0.05 | — | 0.006 | >10 | 0.006 | 0.01 | 0.035 | 0.006 | 0.001 | >25 |
| 16 | 100 | >100 | 0.001 | 2 | 0.002 | >10 | 0.0006 | 0.002 | 0.002 | 0.007 | 0.002 | 7.5 |
| 17 | >100 | >100 | >0.05 | — | >0.05 | — | >0.05 | 0.002 | 0.02 | 0.002 | 0.0006 | 3 |
| 18 | >100 | >100 | 0.003 | 3 | 0.001 | >10 | 0.001 | 0.002 | 0.002 | 0.004 | 0.0003 | 3 |
| 19 | 50 | >100 | 0.002 | 6 | 0.002 | 10 | 0.003 | 0.002 | 0.002 | 0.002 | 0.0006 | 0.75 |
| 20 | 24 | 17 | 0.002 | 6 | 0.003 | >10 | 0.003 | 0.06 | 0.03 | 0.06 | 0.07 | 3 |
| 21 | <10 | 82 | 0.0006 | 6 | 0.003 | >10 | 0.003 | 0.006 | 0.006 | 0.004 | 0.002 | 5 |
| 22 | >100 | >100 | 0.03 | >10 | 0.03 | >10 | 0.03 | 0.07 | 0.09 | 0.08 | 0.002 | 17 |
| 23 | >100 | >100 | 0.003 | >10 | 0.002 | >10 | 0.006 | 0.03 | 0.04 | 0.03 | 0.005 | 17 |
| 24 | >100 | >100 | 0.05 | — | 0.01 | >10 | 0.01 | 0.002 | 0.03 | 0.003 | 0.0005 | 5 |
| 25 | 20 | >100 | 0.001 | 6 | 0.002 | >10 | 0.002 | 0.002 | 0.008 | 0.005 | 0.0006 | 7.5 |
| 26 | 75 | >100 | 0.002 | 6 | 0.03 | >10 | 0.002 | 0.002 | 0.003 | 0.006 | 0.002 | 2.5 |
| 27 | 65 | >100 | 0.006 | 3 | 0.003 | >10 | 0.002 | 0.002 | 0.003 | 0.003 | 0.001 | 4 |
| 28 | <100 | — | 0.002 | 6 | 0.003 | 10 | 0.003 | 0.006 | 0.007 | 0.003 | 0.003 | 2 |
| 29 | >100 | >100 | >0.05 | — | 0.002 | >10 | 0.006 | 0.004 | 0.03 | 0.007 | 0.003 | 17 |
| 30 | >100 | >100 | 0.05 | — | 0.002 | >10 | 0.002 | 0.003 | 0.005 | 0.002 | 0.003 | 17 |
| 31 | >100 | >100 | 0.05 | — | 0.002 | 10 | 0.001 | 0.001 | 0.003 | 0.002 | 0.002 | 7.5 |
| 32 | >100 | >100 | 0.05 | — | 0.002 | >10 | 0.002 | 0.002 | 0.003 | 0.002 | 0.0006 | 2 |
| 33 | 47 | >100 | 0.001 | 10 | 0.006 | >10 | 0.006 | 0.003 | 0.03 | 0.06 | 0.001 | >25 |
| 34 | 42 | >100 | 0.001 | >10 | 0.001 | >10 | 0.003 | 0.001 | 0.05 | 0.08 | 0.007 | >25 |
| 35 | 79 | >100 | 0.003 | 3 | 0.002 | >10 | 0.003 | 0.003 | 0.003 | 0.002 | 0.001 | 7.5 |
| 36 | 75 | >100 | 0.002 | 1 | 0.003 | >10 | 0.002 | 0.003 | 0.003 | 0.003 | 0.001 | 3 |
| 37 | >100 | >100 | >0.05 | — | >0.05 | — | >0.05 | 0.03 | 0.05 | 0.01 | 0.006 | 3 |
| 38 | >100 | >100 | >0.05 | — | >0.05 | — | >0.05 | 0.1 | 0.05 | 0.01 | 0.003 | >25 |
| 39 | >100 | >100 | >0.05 | — | >0.05 | — | >0.05 | 0.01 | 0.006 | 0.01 | 0.006 | 3 |
| 40 | 11 | 61 | 0.0003 | 0.06 | 0.003 | >10 | 0.003 | 0.01 | 0.008 | 0.003 | 0.01 | 2 |
| 41 | >100 | >100 | 0.003 | >10 | 0.001 | >10 | 0.003 | 0.003 | 0.003 | 0.006 | 0.002 | >25 |
| 42 | 51 | <50 | 0.01 | >10 | 0.01 | >10 | 0.01 | 0.001 | 0.03 | 0.003 | 0.002 | 3 |
| 43 | >100 | >100 | 0.001 | 3 | 0.003 | >10 | 0.01 | 0.002 | 0.005 | 0.005 | 0.0006 | 7.5 |
| 44 | >100 | >100 | 0.002 | >10 | 0.002 | >10 | 0.006 | 0.002 | 0.004 | 0.003 | 0.001 | 7.5 |
| 45 | 75 | >100 | 0.003 | >10 | 0.0003 | >10 | 0.001 | 0.002 | 0.004 | 0.001 | 0.0005 | >25 |
| 46 | >100 | >100 | 0.01 | >10 | 0.001 | >10 | 0.03 | 0.01 | 0.07 | 0.01 | 0.005 | 17 |
| 47 | >100 | >100 | 0.006 | 6 | 0.001 | >10 | 0.01 | 0.003 | 0.02 | 0.007 | 0.0001 | 3 |
| 48 | <100 | <100 | 0.003 | 6 | 0.003 | >10 | 0.01 | <0.003 | 0.004 | 0.0007 | 0.0007 | 3 |
| 49 | 100 | >100 | 0.002 | 6 | 0.002 | 10 | 0.002 | 0.003 | 0.003 | 0.005 | <0.003 | 0.75 |
| 50 | >100 | >100 | 0.0006 | >10 | 0.003 | >10 | 0.03 | 0.004 | 0.01 | — | 0.003 | 4 |
| 51 | >100 | >100 | 0.003 | >10 | 0.001 | >10 | 0.001 | 0.015 | 0.03 | — | — | >25 |

TABLE II-continued

| Cmpd. No. | HF, μg C | F* | BA C, % | S, ppm | (LD$_{50}$) 2-SM A, % | S, ppm | E, % | TBW, % C | E | BAW, % | CL, % | Diabrotica, ppm (soil) |
|---|---|---|---|---|---|---|---|---|---|---|---|---|
| 52 | 87 | >100 | 0.003 | 6 | 0.003 | >10 | >0.05 | 0.01 | 0.03 | — | — | 4 |
| 53 | >100 | >100 | 0.006 | 6 | 0.006 | >10 | 0.05 | 0.0075 | 0.01 | — | — | 4 |
| 54 | 76 | >100 | >0.05 | >10 | 0.003 | >10 | 0.006 | 0.005 | 0.03 | — | — | 7.5 |
| 55 | >100 | >100 | 0.006 | >10 | 0.003 | >10 | 0.03 | 0.006 | 0.003 | 0.1 | 0.006 | 2 |
| 56 | 39 | >100 | 0.006 | 10 | 0.002 | >10 | 0.01 | 0.05 | 0.1 | >0.1 | 0.03 | >25 |
| 57 | <100 | <100 | 0.01 | 6 | 0.003 | 10 | 0.01 | 0.01 | 0.004 | 0.04 | 0.03 | 2 |
| 58 | >100 | >100 | 0.001 | 2 | 0.001 | >10 | 0.006 | 0.0025 | 0.002 | 0.04 | 0.0006 | 2 |
| 59 | <100 | <100 | 0.001 | >10 | 0.0003 | >10 | 0.001 | 0.006 | 0.008 | 0.015 | 0.006 | 2 |
| 60 | <100 | <100 | 0.002 | >10 | 0.001 | >10 | 0.006 | 0.004 | 0.008 | 0.03 | 0.002 | 2 |
| 61 | 55 | >100 | 0.001 | 6 | 0.03 | >10 | 0.03 | 0.07 | 0.03 | 0.05 | 0.005 | 17 |
| 62 | >100 | >100 | 0.01 | 10 | 0.01 | >10 | 0.01 | 0.005 | 0.02 | 0.03 | 0.0007 | >25 |

Key:
C = Contact Test
F = Fumigant Test
S = Systemic Test
E = Test on eggs
A = Test on adults
*Per 285 ml volume container Selected compounds were evaluated on two other insects—the German cockroach and lygus bug, by the following procedures.

German Cockroach [Blatella germanica (Linn.)]

Test compounds were diluted in a 50-50 acetone-water solution. Two ml of the solution was sprayed through a hand spray gun into circular cardboard cages containing 10 one-month old German cockroach nymphs. The test cages were covered on the bottom with callophane and on the top with tulle netting. Percent mortality was recorded 4 days later. Test concentrations ranged from 0.1% downward. The LD-50 values are expressed below in Table III under the heading "GR" in terms of percent of the test compound in the sprayed solution.

Lygus Bug [Lygus hesperus (Knight)]

Test compounds were diluted in a 50-50 acetone-water solution. Two ml of the solution was sprayed through a hand spray gun into circular cardboard cages containing one green bean pod and 10 adult lygus bugs. The test cages were covered on the bottom with cellophane and on the top with tulle netting. Percent mortality was recorded 48 hours later. Test concentrations ranged from 0.05% downward. The LD-50 values are expressed below in Table III under the heading "LB" in terms of percent of the test compound in the sprayed solution.

TABLE III

| Compound Number | (LD$_{50}$) GR, % | LB, % |
|---|---|---|
| 2 | 0.03 | >0.05 |
| 3 | 0.025 | 0.03 |
| 17 | 0.03 | 0.005 |
| 18 | 0.035 | 0.008 |
| 21 | 0.01 | 0.006 |
| 22 | 0.1 | >0.05 |

In practice, a pure compound can be used as an insecticide. However, in general, the compounds are first formulated with one or more inert (i.e. non-chemically reactive, plant compatible or herbicidally inert) carriers or diluents suitable for insecticidal use, before being applied.

The compositions or formulations, including a compound as described herein, may take any one of a number of solid or liquid forms. Examples of solid forms are dusts, granules, tablets, powders and the like. Examples of liquid forms are emulsions, solutions, suspensions, flowables, emulsifiable concentrates and pastes. Such compositions may contain, in addition to the active compound or compounds, various carriers or diluents; surface-active agents (wetting agents, dispersing agents and/or emulsifying agents); solvents (water, or organic solvents such as aromatic solvents or chlorinated aliphatic solvents); adhesives; thickeners; binders; antifoaming agents; and other substances as mentioned herein. Solid carriers or diluents included in such compositions or formulations may include, for example, ground natural minerals such as kaolins, alumina, calcined diatomaceous earth, calcium carbonate, silica, kieselguhr, clays, etc.; ground synthetic minerals such as various silicates and alumino-silicates and ground vegetable products such as bark, cornmeal, sawdust, cellulose powder and the like. Compositions containing sorptive clays will usually also contain a stabilizer, such as glycol, to prevent or minimize degradation of the active ingredient.

To manufacture solid compositions, the active substances are mixed with solid carriers or diluents such as those mentioned above and the mixture is ground to the appropriate size. Granules can be manufactured by dissolving an active compound in an organic solvent and applying the mixture, for example, by atomization, onto an absorptive granulated inert material, such as silica. Adhesives may be utilized to assist in the incorporation of the compound onto the solid particles.

Wettable powders and pastes are obtained by mixing and grinding an active compound with one or more dispersing agents and/or solid carriers or diluents. Also included may be wetting agents and/or dispersing agents, for example, lignins, methyl cellulose, naphthalenesulfonic acid derivatives, fatty alcohol sulfates and various types of akali and alkaline earth metal salts of fatty acids.

Emulsifiable concentrates are generally obtained by dissolving the active compound in an organic solvent, for example, butanol, cyclohexanone, xylenes, or higher boiling aromatic hydrocarbons. To obtain suspensions or emulsions in water, wetting agents may also be added.

Flowables are prepared by mixing an active compound with one or more dispersing agents and/or solid additives, and a liquid (which may be water or an organic solvent) in which the active compound is relatively insoluble, and grinding the mixture.

Both liquid and solid compositions may be in microcapsule or encapsulated form, to permit release of the enclosed active compound at a controlled rate over a period of time. Liquid compositions of this type contain encapsulated droplets of approximately 1–50 microns in diameter, including the active compound and optionally a solvent. The encapsulating material is an inert porous membrane of a polymeric material.

Solid encapsulated compositions generally take the form of granules, in which the liquid containing the active component is trapped in the pores of the granular support by a porous polymeric membrane through which the active ingredient may migrate at a controlled rate, or which membrane breaks down at a controlled rate to permit escape of the active ingredient.

Typical encapsulating materials include natural and synthetic rubbers, cellulosic materials, styrene-butadiene copolymers, polyacrylonitriles, polyacrylates, polyamides, polyisocyanates, polyurethanes, mixed copolymers of the foregoing and starch xanthates.

It is possible to use highly concentrated liquid compositions containing up to about 95% by weight of the active compound, or even the 100% active compound alone, when applying the compound in the form of a finely divided liquid by use of various atomizing equipment, for example by airplane spraying techniques. For other purposes, however, the various types of compositions which can be utilized for these compounds will contain varying amounts of the compound according to the type of composition and the intended use.

In general, insecticidal compositions may contain from 5 to 95% of the active compound, more preferably from 10 to 85%. Some typical compositions will contain an active compound as follows: wettable powders: 25 to 80% active compound; oil suspensions, emulsions, solutions, flowables, and emulsifiable concentrates: 5 to 85% active compound; aqueous suspensions: 20 to 50% active compound; dusts and powders: 5 to 20% active compound; granules and pellets: 5 to 20% active compound.

In addition to the active compound and the various agents utilized in preparing compositions and formulations mentioned, such compositions may also contain one or more other active compounds of the type mentioned herein as well as other active pesticidal agents, such as herbicides, fungicides, insecticides, acaricides, nematocides, bactericides, and plant growth regulators. Such compounds may also contain soil disinfectants or fumigants and may further contain fertilizers, thus making it possible to provide multi-purpose compositions containing one or more of the active compounds described herein as well as, optionally, other pesticides and also fertilizers, all intended and formulated for use at the same locus.

Control of insect pests is accomplished by applying a composition containing an insecticidally effective amount of an active compound as described herein to the insect, to a locus at which insecticidal control is desired, or to food sources (including seeds) on which the insects feed. For use in the last mentioned manner it is preferable to utilize a compound which is not volatile. Thus, control may be achieved by direct application of the active compounds to the insects and indirectly by application of the compounds to a locus to be protected (such as crop lands, grass ranges and forests), to a source of food for insects or to other insect habitats (for example, breeding or swarming areas). The rates of application of the active compound, and the concentration applied, will vary according to whether the compound or composition is being directly applied to the insect or indirectly, to a locus, food or habitat. In the latter case the rate of the application, depending on the nature of the insect or insects to be controlled, and the plant environment, will generally vary from about 0.01 to about 100 pounds per acre (about 0.011 to about 111 kg/ha).

It should be noted that the active compound need not be insecticidally active per se to effect insect control. The purposes of this invention are fully served if such compounds are rendered active by external influences, such as light or heat, or by some physiological action which occurs when the compound is ingested into the body of the insect.

Compositions containing one or more of the active compounds described, in an insecticidally effective amount, may be applied to the plant, locus or insect habitat in any conventional manner.

When used in connection with crop or other plant protection, application may be made in a preventive (i.e. before infestation) or eradicative manner (i.e., after infestation). Thus, powders and various liquid compositions containing the active compound can be applied by the use of powder dusters, boom and hand sprayers and spray dusters, or applied from airplanes as dusts or sprays. When applied in the latter method they may be effective in very low dosages.

Compositions including active compounds may also be applied by addition to irrigation waters supplied to the field to be treated. This method of application permits penetration of the compounds into the soil as the water is absorbed therein.

Compositions including active compounds may additionally be used to protect plant seeds from being attacked by soil-borne insect pests after planting and during germination, by applying the composition to the seeds as a seed dressing. This is performed generally by mixing the seeds with an active composition in either liquid or solid form (preferably liquid) in a suitable mixing apparatus. Liquid compositions for this purpose may contain an adhesive or sticking agent, such as methyl cellulose, ethyl cellulose, etc., to assist the composition in adhering to the seed. If a solid composition is utilized for this purpose, an adhesive agent may be sprayed on the seeds during or after mixing.

For use as a soil insecticide, the active compound, or compositions containing it, may be mixed with the soil in any conventional manner, before, during or after planting of the plant seeds. Liquid compositions may be applied by spraying onto the surface or by incorporation in irrigation or sprayed water. Solid or liquid compositions containing an active compound may be incorporated into the soil prior to or during planting by discing, plowing or other mixing operations, in order to locate the active ingredient below the surface of the soil so as to be most effective in controlling undesirable larvae.

Some examples of compositions containing the active compounds of this invention are:

| Component | Weight % |
| --- | --- |
| Composition A: Granular Solid | |
| Compound 1 | 10 |

| Component | Weight % |
| --- | --- |
| attapulgite clay granules | 85 |
| triethylene glycol | 5 |
| Total | 100% |
| Composition B: Wettable Powder | |
| Compound 11 | 80 |
| wetting agent (sodium dialkyl-naphthalene sulfonate) | 1 |
| dispersing agent (sodium lignosulfonate) | 4 |
| diluent (aluminum magnesium silicate) | 15 |
| Total | 100% |
| Composition C: Dilute Solution | |
| Compound 16 | 5 |
| solvent (xylene) | 95 |
| Total | 100% |
| Composition D: Emulsifiable Concentrate | |
| Compound 25 | 50 |
| Emulsifier (blend of metal sulfonates and polyoxyethylene ethers) | 10 |
| solvent (xylene) | 40 |
| Total | 100% |
| Composition E: Concentrated Solution | |
| Compound 40 | 90 |
| solvent (xylene) | 10 |
| Total | 100% |

What is claimed is:

1. A method for controlling insects comprising applying to an insect, the locus of an insect or a locus at which insecticidal control is desired, an insecticidally effective amount of a compound having the formula

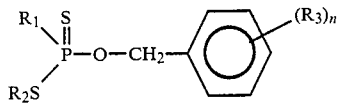

in which $R_1$ is methyl or ethyl; $R_2$ is $C_1$–$C_6$ alkyl; $R_3$ is halogen, $C_1$–$C_4$ alkyl, trifluoromethyl, thio-($C_1$–$C_4$ alkyl) or phenoxy, and n is 0, 1 or 2; provided that if $R_2$ is methyl, then $R_1$ is methyl.

2. A method according to claim 1 in which $R_2$ is $C_3$–$C_6$ alkyl.

3. A method according to claim 1 in which $R_2$ is $C_4$–$C_6$ alpha-branched alkyl.

4. A method according to claim 3 in which $R_2$ is secondary butyl.

5. A method according to claim 3 in which $R_2$ is tertiary butyl.

6. A method according to claim 1 in which n is 0.

7. A method according to claim 1 in which $R_2$ is alpha-branched $C_4$–$C_6$ alkyl.

8. A method according to claim 1 in which n is 1 and $R_3$ is halogen.

9. A method according to claim 8 in which $R_2$ is alpha-branched $C_4$–$C_6$ alkyl.

10. A method according to claim 9 in which $R_3$ is chlorine.

11. A method according to claim 9 in which $R_3$ is bromine.

12. A method according to claim 9 in which $R_3$ is fluorine.

13. A method according to claim 1 in which n is 2 and $R_3$ is halogen.

14. A method according to claim 13 in which $R_3$ is chlorine.

15. A method according to claim 13 in which $R_3$ is fluorine.

16. A method according to claim 13 in which $R_3$ represents one chloride and one fluorine substitution.

17. A method according to claim 1 in which n is 1 and $R_3$ is $C_1$–$C_4$ alkyl.

18. A method according to claim 17 in which $R_2$ is $C_4$–$C_6$ alpha-branched alkyl.

19. A method according to claim 18 in which $R_3$ is methyl.

20. A method according to claim 18 in which $R_3$ is tertiary butyl.

21. A method according to claim 1 in which n is 2 and $R_3$ is methyl.

22. A method according to claim 1 in which n is 1 and $R_3$ is trifluoromethyl.

23. A method according to claim 22 in which $R_2$ is $C_4$–$C_6$ alpha-branched alkyl.

24. A method according to claim 1 in which n is 1 and $R_3$ is thiomethyl.

25. A method according to claim 1 in which the compound is applied to soil to control soil-borne insects.

26. A method according to claim 1 in which the insect to be, controlled is a lepidopterous insect.

27. A method according to claim 26 in which the compound is applied to foliage of a plant.

28. A compound having the formula

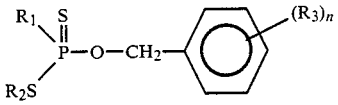

in which $R_1$ is methyl or ethyl; $R_2$ is $C_1$–$C_6$ alkyl; $R_3$ is halogen, $C_1$–$C_4$ alkyl, trifluoromethyl, thio-($C_1$–$C_4$ alkyl) or phenoxy, and n is 0, 1 or 2; provided that if $R_2$ is methyl, then $R_1$ is methyl.

29. A compound according to claim 28 in which $R_2$ is $C_3$–$C_6$ alkyl.

30. A compound according to claim 28 in which $R_2$ is $C_4$–$C_6$ alpha-branched alkyl.

31. A compound according to claim 30 in which $R_2$ is secondary butyl.

32. A compound according to claim 30 in which $R_2$ is tertiary butyl.

33. A compound according to claim 28 in which n is 0.

34. A compound according to claim 33 in which $R_2$ is $C_4$–$C_6$ alpha-branched alkyl.

35. A compound according to claim 28 in which n is 1 and $R_3$ is halogen.

36. A compound according to claim 35 in which $R_2$ is $C_4$–$C_6$ alpha-branched alkyl.

37. A compound according to claim 36 in which $R_3$ is chlorine.

38. A compound according to claim 36 in which $R_3$ is bromine.

39. A compound according to claim 36 in which $R_3$ is fluorine.

40. A compound according to claim 28 in which n is 2 and $R_3$ is halogen.

41. A compound according to claim 40 in which $R_3$ is chlorine.

42. A compound according to claim 40 in which $R_3$ is fluorine.

43. A compound according to claim 40 in which $R_3$ represents one chlorine and one fluorine substitution.

44. A compound according to claim 28 in which n is 1 and $R_3$ is $C_1$-$C_4$ alkyl.

45. A compound according to claim 44 in which $R_2$ is $C_4$-$C_6$ alpha-branched alkyl.

46. A compound according to claim 44 in which $R_3$ is methyl.

47. A compound according to claim 44 in which $R_3$ is tertiary butyl.

48. A compound according to claim 28 in which n is 2 and $R_3$ is methyl.

49. A compound according to claim 28 in which n is 1 and $R_3$ is trifluoromethyl.

50. A compound according to claim 49 in which $R_2$ is $C_4$-$C_6$ alpha-branched alkyl.

51. A compound according to claim 28 in which n is 1 and $R_3$ is thiomethyl.

52. An insecticidal composition comprising (a) an insecticidally effective amount of a compound having the formula

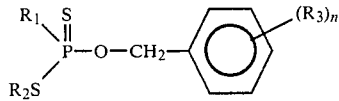

in which $R_1$ is methyl or ethyl; $R_2$ is $C_1$-$C_6$ alkyl; $R_3$ is halogen, $C_1$-$C_4$ alkyl, trifluoromethyl, thio-($C_1$-$C_4$ alkyl) or phenoxy, and n is 0, 1 or 2; provided that if $R_2$ is methyl, then $R_1$ is methyl and (b) an insecticidally suitable diluent or carrier.

* * * * *